United States Patent
Joseph

(10) Patent No.: US 7,620,279 B2
(45) Date of Patent: Nov. 17, 2009

(54) POLYURETHANE LIGHT GUIDES

(75) Inventor: Edmond Kenneth Joseph, Burleigh (AU)

(73) Assignee: Poly Optics Australia Pty. Ltd., Burleigh Queensland (AU)

( * ) Notice: Subject to any disclaimer, the term of this patent is extended or adjusted under 35 U.S.C. 154(b) by 0 days.

(21) Appl. No.: 11/721,649

(22) PCT Filed: Dec. 16, 2005

(86) PCT No.: PCT/AU2005/001913

§ 371 (c)(1),
(2), (4) Date: Oct. 1, 2007

(87) PCT Pub. No.: WO2006/063414

PCT Pub. Date: Jun. 22, 2006

(65) Prior Publication Data

US 2008/0089088 A1    Apr. 17, 2008

(30) Foreign Application Priority Data

Dec. 17, 2004  (AU)  .............. 2004907166
Oct. 19, 2005  (AU)  .............. 2005905775

(51) Int. Cl.
    G02B 6/02    (2006.01)
(52) U.S. Cl. ............... 385/123; 385/125; 385/141; 385/143; 385/145; 385/901
(58) Field of Classification Search ........... 385/12, 385/123, 125, 147, 901, 141, 143, 145
See application file for complete search history.

(56) References Cited

U.S. PATENT DOCUMENTS

| 4,422,719 | A | * | 12/1983 | Orcutt ..................... 385/123 |
| 4,466,697 | A |   | 8/1984  | Daniel ..................... 350/96.3 |
| 4,830,461 | A |   | 5/1989  | Ishiharada et al. ....... 350/96.29 |
| 4,872,837 | A |   | 10/1989 | Issalene et al. ............ 433/29 |
| 4,893,897 | A |   | 1/1990  | Parker et al. ............ 350/96.34 |
| 4,909,594 | A |   | 3/1990  | Haese et al. ............ 350/96.29 |
| 5,334,206 | A | * | 8/1994  | Daikuzono ..................... 606/7 |
| 5,431,647 | A | * | 7/1995  | Purcell et al. ................ 606/16 |
| 5,542,017 | A |   | 7/1996  | Koike ..................... 385/123 |
| 6,551,346 | B2 | * | 4/2003 | Crossley ..................... 607/88 |
| 7,356,225 | B2 | * | 4/2008 | Loebel ..................... 385/38 |
| 2004/0058733 | A1 | | 3/2004 | Hussaini et al. ............ 463/47 |
| 2005/0221250 | A1 | | 10/2005 | Kanca ..................... 433/29 |

(Continued)

FOREIGN PATENT DOCUMENTS

JP    08-117255    5/1996

(Continued)

OTHER PUBLICATIONS

European Search Report EP 05 81 8561, Feb. 17, 2009.

*Primary Examiner*—Brian M Healy
(74) *Attorney, Agent, or Firm*—Duane Morris LLP

(57) ABSTRACT

A light guide (1) formed from an unclad flexible polyurethane fiber produces significant side scattering (2) over distances of up to several meters. The polyurethane fiber is in the form of a solid fiber or a tube and may comprise light scattering particles. The polyurethane fiber may comprise a transparent flexible polyurethane UV resistant outer cladding. Embodiments include illuminated shoe laces, a power cord safety indicator, an illuminated dental suction tube and a dental curing tip.

16 Claims, 3 Drawing Sheets

U.S. PATENT DOCUMENTS

2006/0018596 A1* 1/2006 Loebel ................ 385/38
2008/0089088 A1* 4/2008 Joseph ................ 362/573

FOREIGN PATENT DOCUMENTS

| KR | 2004/0090676 | 10/2004 | | |
|----|--------------|---------|---|---|
| WO | WO 99/42270 | 8/1999 | ............ | 385/123 X |
| WO | WO 02/095289 | 11/2002 | | |
| WO | WO 2004/053531 | 6/2004 | | |

* cited by examiner

POLYURETHANE LIGHT GUIDES

FIELD OF THE INVENTION

This invention relates to flexible side-illuminating optical fibres or light guides. In particular, it relates to light guides formed from polyurethane.

BACKGROUND TO THE INVENTION

Optical fibres are being used in a wide variety of applications. The majority of these applications employ the optical fibres for their light transmitting properties. It is known that coherent optical radiation from a laser source can be transmitted along a suitable optical fibre for many hundreds of kilometers.

In contrast to the transmission properties, optical fibres have also been used for their loss properties. One example is U.S. Pat. No. 4,830,461 assigned to Bridgestone Corporation. This patent describes a pressure sensor made from an optical fibre with a light emitting means at one end and a light receiving means at the other end. When pressure is applied to the fibre a deformation occurs which causes transmission loss which is detected by the light receiving means. The applied pressure can be calculated from the measured decrease in signal.

Another field of use of optical fibres is in novelty applications. In our co-pending published international application number WO 02/095289 we describe a side-scattering light guide that has a range of uses including decorative lighting, advertising and illuminated clothing. This last application has proven to be of particular interest, but presents a number of difficulties that have heretofore not been addressed. In particular, light guides for use in clothing, such as illuminated shoe laces, must be very flexible but maintain reasonable light transmission properties for up to a meter.

Suitable light guides have not been produced. The existing light guides are either too brittle for the application or too lossy when bent to a desired configuration.

OBJECT OF THE INVENTION

It is an object of the present invention to provide a flexible light guide that provides side illumination.

Further objects will be evident from the following description.

SUMMARY OF THE INVENTION

In one form, although it need not be the only or indeed the broadest form, the invention resides in a light guide formed from an unclad flexible polyurethane fibre.

Surprisingly the inventor has found that an unclad polyurethane light guide produces significant side scattering over distances of up to several meters.

Preferably, the polyurethane fibre is a solid fibre, but the fibre may also be a tube.

The polyurethane fibre may further comprise light scattering particles.

Suitably, the flexible polyurethane light guide is extruded under non-optimum conditions to produce imperfections in the light guide.

The method may include extruding the light guide at a rate that is too slow or too fast compared with conventional extruding parameters.

In another form, the invention resides in an illuminated shoe lace comprising an unclad flexible polyurethane extruded fibre and one or more light emitting diodes coupling light into said fibre.

In a further form, the invention resides in a safety indicator for a power cord comprising an unclad flexible polyurethane extruded tube and one or more light emitting diodes coupling light into said fibre.

In another form, the invention resides in an illuminated dental suction tube comprising an unclad polyurethane extruded tube and one or more light emitting diodes coupling light into said tube for the illumination of a patient's mouth and for the extraction of fluids from the patient's mouth through the tube.

The illuminated dental suction tube is preferably flexible, but may alternatively be semi-rigid or rigid.

In a further form, the invention resides in a dental curing tip comprising an unclad polyurethane extruded solid fibre and one or more light sources coupling blue light into the fibre for curing fillings in teeth.

The unclad polyurethane extruded solid fibre may be flexible, semi-rigid or rigid.

In a yet further form, the invention resides in a light guide formed from a transparent flexible polyurethane inner fibre having a transparent flexible polyurethane outer cladding, wherein said inner fibre is susceptible to deterioration caused by ultra-violet (UV) radiation and said outer cladding is resistant to deterioration caused by ultra-violet (UV) radiation.

Suitably, the inner fibre and outer cladding are co-extruded.

Preferably, the inner fibre and outer cladding are coaxial.

Suitably, the outer cladding has a thickness less than the thickness of the inner fibre.

Preferably, the thickness of the outer cladding is substantially less than the thickness of the inner fibre.

Further features of the present invention will become apparent from the following detailed description.

BRIEF DETAILS OF THE DRAWINGS

To assist in understanding the invention preferred embodiments will now be described with reference to the following figures, which are provided by way of example only, in which.

DETAILED DESCRIPTION OF THE DRAWINGS

Figure 1:
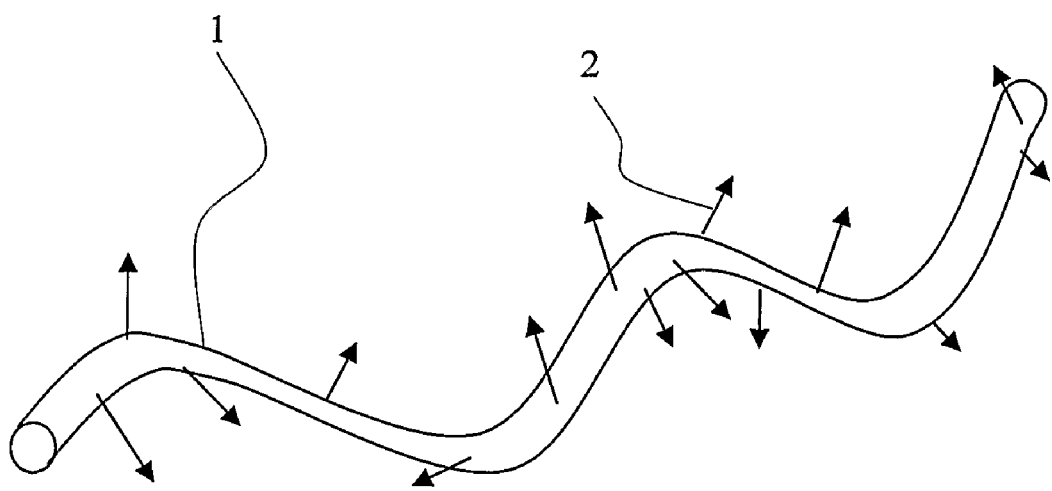
FIG. 1 shows a side-scattering polyurethane light guide according to a first embodiment of the present invention.

In describing different embodiments of the present invention common reference numerals are used to describe like features.

FIG. 1 is a sketch of a piece of side-scattering polyurethane light guide 1. The light guide is flexible and side scatters light over the entire length, as indicated by the arrows 2. Polyurethane has been used as a protective coating for optical fibres and other applications, but it has not been previously considered as a side illumination light guide. However, the inventor has found that under appropriate extruding or casting conditions, a flexible polyurethane light guide has light leakage properties that make it useful for many novelty applications The light guide 1 is typically extruded using known extrusion techniques, although it may also be cast in a rod or in sheet form. For most applications an elongate fibre is preferred. The extrusion conditions are set to be too quick or too slow compared with conventional extruding parameters. This causes some yellowing of the extruded guide but also leads to scattering due to imperfections in the guide. In addition, the guide is used unclad so that light leaks from the guide over its length.

A typical length of the light guide is less than 1 meter and the diameter is up to a few millimeters and may be as small as one hundred microns. In most applications the light source is a light emitting diode (LED), as is known in the art. As will be appreciated by persons skilled in the field other light sources will be possible, but they may not be suitable in the majority of applications.

Polyurethane is produced from a cross-linking reaction of an acrylic resin containing an amine group. The monomer is catalyzed by polyisocyanate. Various plasticizers and accelerators are normally mixed with the monomer to control the properties of the polyurethane. The light transmission and side-leakage properties can be adjusted by control of the cross-linking reaction. This control may be related to the purity of the reacting chemicals. Careful control of the reaction chemicals will lead to light transmission over a greater length of fibre and less side-leakage. The reaction conditions also impact the fibre properties. For example, extruding at a rate that is too slow or too fast will lead to shorter transmission lengths and more side-leakage.

Figure 2:
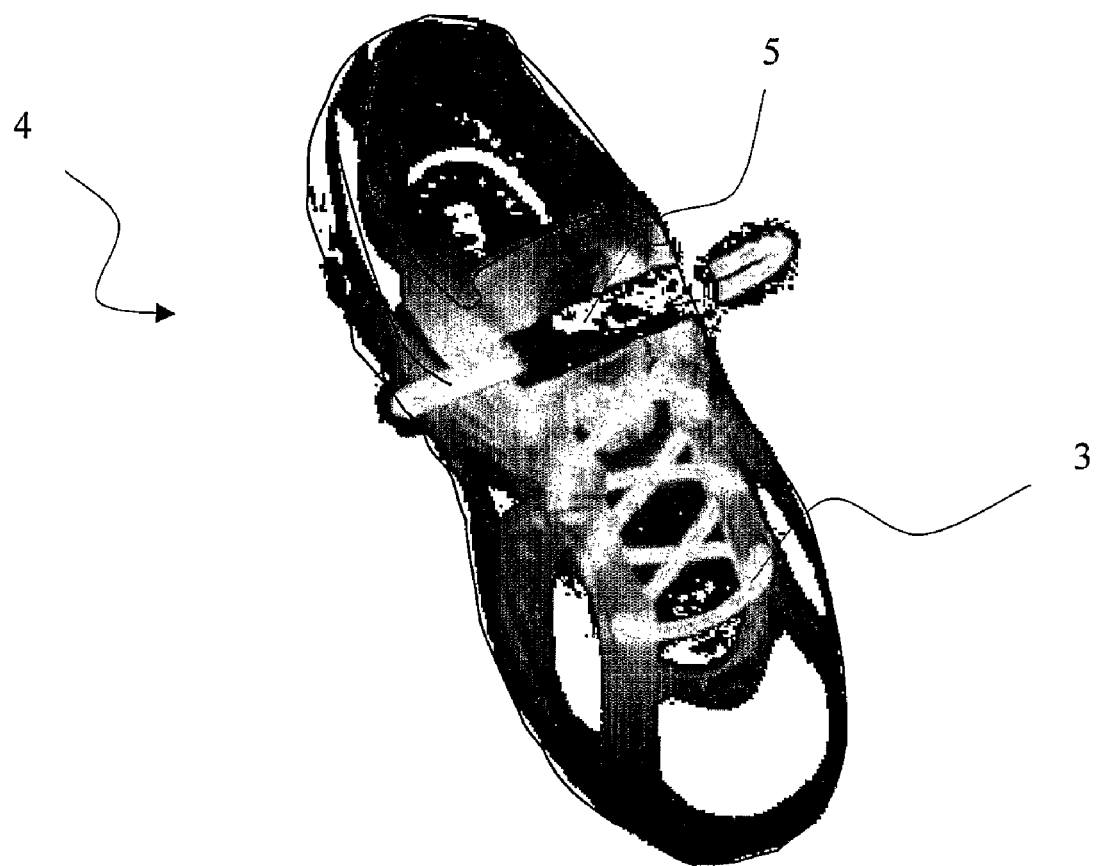
FIG. 2 shows the light guide of FIG. 1 laced into a pair of shoes.

As foreshadowed above, one particular application of the polyurethane light guide is in clothing and particularly in footwear. An example of a use of a light guide such as that of FIG. 1 is shown in FIG. 2. The light guide 3 is laced into a shoe 4 and the shoe lace glows. The illumination is provided by a pair of light emitting diodes (not visible) contained in a housing 5 at the top of the shoe lace. The housing also contains a battery (not visible) to power the diodes. Typically, a light guide 3 is laced into each shoe of a pair of shoes.

Figure 3:
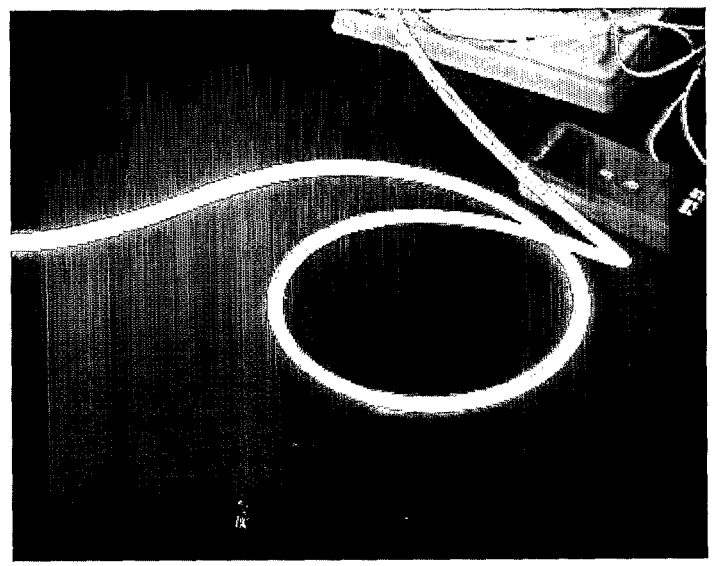
FIG. 3 shows a photograph of a piece of the light guide.
Figure 4:
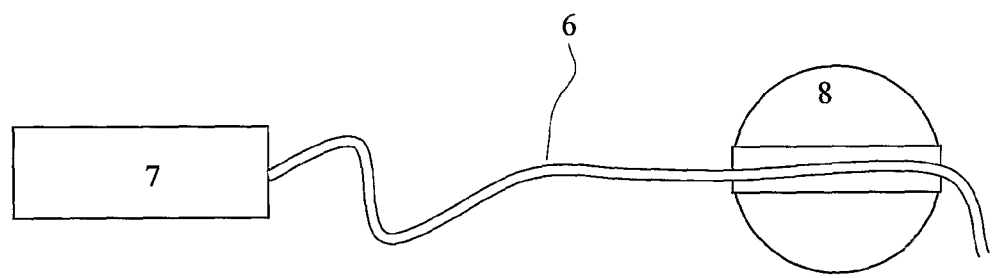
FIG. 4 shows an arrangement for measuring the amount of light scattered from the light guide of FIG. 3.

To demonstrate the performance of a typical polyurethane light guide the inventor has measured the intensity of light lost through the sides of a typical sample compared to the intensity of light injected. A photograph of the light guide is shown in FIG. 3 and the experimental set-up is shown in FIG. 4. In FIG. 4 a light guide 6 is coupled to a 150 watt metal halide light source 7. An integrating sphere with photodetector 8 measures the amount of light leaking from the side of the fibre.

In order to exemplify the side-leakage properties of the urethane light guide (ULG), a sample piece was compared to a side-light fibre (SLF) produced according to the process in our earlier international patent application WO 99/59804. In each case a 1.5 meter length of 7 mm diameter fibre was illuminated by five different colours (white, blue, green, yellow, orange) from the light source 7. A reading of side-leakage light was made at the end, the halfway point and the quarter way point for each fibre sample for each of the five colours. The following tables summarise the measurements:

TABLE 1

SLF SAMPLE—1.5 m, 7 mm diameter

PLACEMENT ON FIBRE LENGTH FROM DRIVER

| | End (150 cm) | | ½ (75 cm) | | ¼ (35 cm) | |
|---|---|---|---|---|---|---|
| | Output | Colour | Output | Colour | Output | Colour |
| White | 2440 | White | 33 | White | 33 | White |
| Blue | 905 | Blue | 8 | Blue | 14 | Blue |
| Green | 783 | Green | 6 | Green | 11 | Green |
| Yellow | 1452 | Yellow | 10 | Yellow | 24 | Yellow |
| Orange | 1130 | Orange | 7 | Orange | 16 | Orange |

TABLE 2

ULG SAMPLE—1.5 m, 7 mm diameter

PLACEMENT ON FIBRE LENGTH FROM DRIVER

| | End (150 cm) | | ½ (75 cm) | | ¼ (35 cm) | |
|---|---|---|---|---|---|---|
| | Output | Colour | Output | Colour | Output | Colour |
| White | 26 | Deep orange | 48 | Orange | 155 | Yellow |
| Blue | 1 | Very pale green | 4 | Lemon green | 40 | Pale Green |
| Green | 3 | Very pale green | 8 | Pale green | 46 | Green |
| Yellow | 22 | Pale orange | 38 | Amber | 132 | Yellow |
| Orange | 23 | Deep orange | 34 | Orange | 98 | Orange |

The inventor has found that the degree of light leakage from the unclad polyurethane light guide is suitable for many applications. As is evident from Table 2, much of the light leaks from the fibre within less than a meter. There is also a colour shift towards the orange evident. If an even greater intensity of side illumination is desired it can be achieved according to the process of our co-pending application mentioned above by the inclusion of scattering particles.

Figure 5:
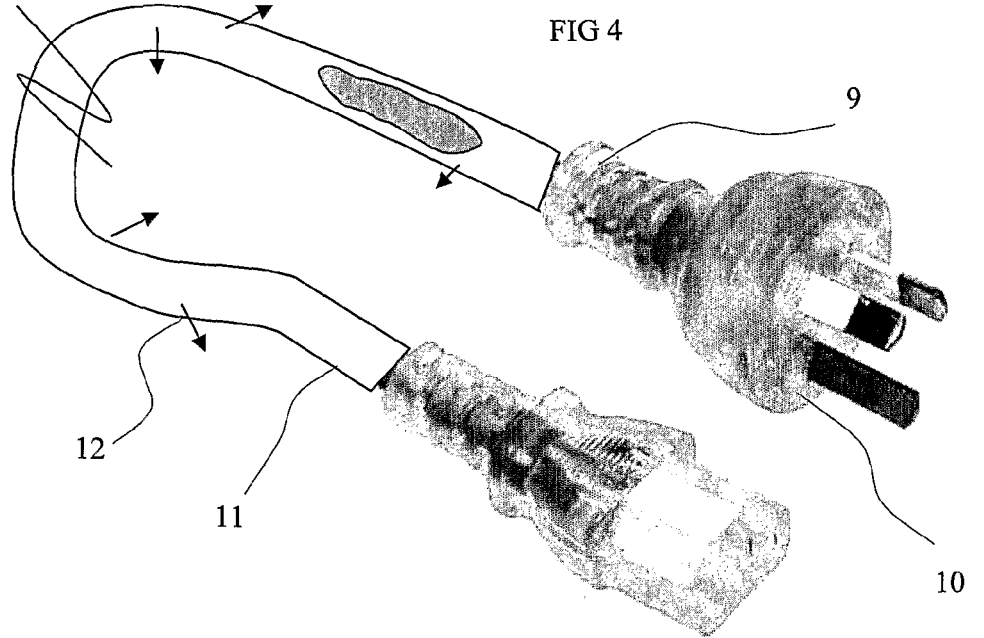
FIG. 5 shows a urethane light guide applied to a power cord.

It is generally anticipated that the polyurethane light guide will be formed as a continuously extruded solid rod. However, the light guide can also be extruded as a tube with similar light distribution properties. One particular application when extruded as a tube is as a safety covering for a power cord 9, as shown in FIG. 5. In this application a light emitting diode (not visible) in the plug 10 of the power cord provides illumination to the polyurethane tube 11 that is conveyed by the tube 11 which is formed as a jacket around the power cord 9. When the power cord is plugged into a power outlet the light emitting diode is powered and the polyurethane jacket glows 12 to give a visual indication along the full length of the cord.

The light guide can also be produced as a cast sheet or extruded into different continuous shapes, such as an oval, a star, or a complex shape that would slide easily into a track.

Figure 6:
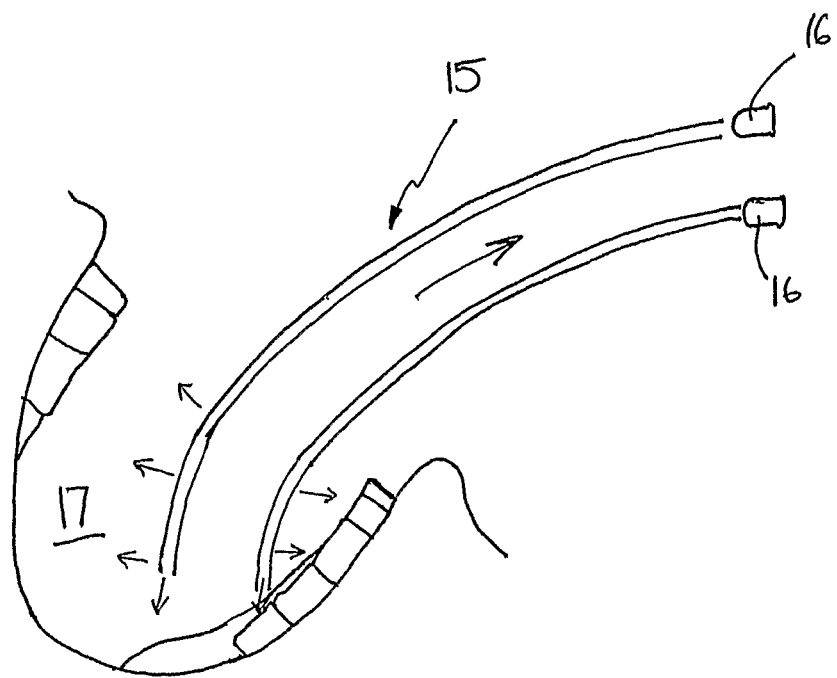
FIG. 6 shows the light guide in the form of a dental suction tube.

Another application of the light guide of the present invention when extruded as a tube is as an illuminated dental suction tube 15, as shown in FIG. 6. In this application, one or more light emitting diodes 16 provide illumination that is conveyed by the polyurethane tube 15 into the mouth 17 of a patient. By virtue of both the light transmission properties (indicated by the smaller longitudinal arrows at the end of tube 15 in FIG. 6) and side scattering properties (indicated by the smaller transverse arrows in FIG. 6) of the light guide, the suction tube 15 provides illumination to the whole mouth as well as at the end of the light guide where fluid is to be extracted from the patient's mouth 17. Fluid is extracted from the mouth through the hollow tube 15 (indicated by the larger longitudinal arrow in FIG. 6) to a receptacle (not shown) in a conventional manner. The unclad the polyurethane tube 15 can be flexible, semi-rigid or rigid.

Hence, a dentist's assistant/nurse is assisted by the illuminated suction tube 15 because the location from which fluid is to be extracted is illuminated due to light transmission. Additionally, the dentist is assisted by the illuminated suction tube 15 because a large proportion of the mouth is locally illuminated due to side scattering, which helps to address the problem of shadows in the mouth encountered with conventional overhead dental light sources.

The suction tube 15 will typically be about 150 mm in length such that it is of sufficient length to reach inside the mouth and connect with the receptacle for fluid extraction, but not too long to render it cumbersome and unwieldy. Other lengths of tube may, of course, be used. The suction tube 15 may be disposable or may be autoclaved for re-use.

The inventor has recognized that an alternative embodiment of the dental suction tube 15 can be formed from another light transmitting material, such as polycarbonate, which can be extruded or injection molded in the form of a tube to the desired length.

A further application of the light guide of the present invention, also in the dental field, is in a dental curing tip comprising an unclad polyurethane extruded solid fibre and one or more light sources coupling blue light into the fibre for curing fillings in teeth. The unclad polyurethane extruded solid fibre is preferably flexible, but can be semi-rigid or rigid.

Figure 7:
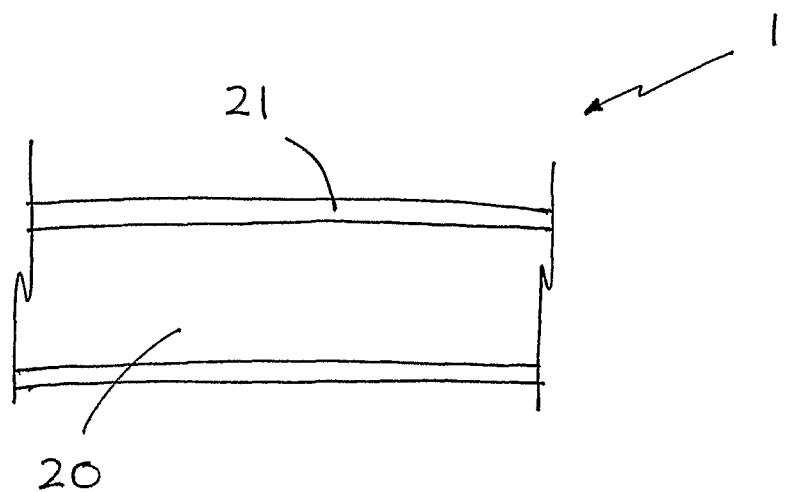
FIG. 7 shows a side-scattering polyurethane light guide according to a second embodiment of the present invention.

With reference to FIG. 7, according to another embodiment, the light guide 1 is formed from a transparent flexible polyurethane inner fibre 20 having a transparent flexible polyurethane outer cladding 21. The inner fibre is susceptible to deterioration caused by ultra-violet (UV) radiation and said outer cladding 21 is resistant to deterioration caused by ultra-violet (UV) radiation.

In the aforementioned production process in which the cross-linking reaction is carefully controlled, the UV inhibitors are removed to achieve the desired transmission and side-leakage properties. Therefore, the resulting light guide is susceptible to deterioration when exposed to UV radiation, in particular in outdoor applications.

To maintain the transmission and side-leakage properties of the light guide, but achieve a UV resistant light guide, the inventor has invented the aforementioned light guide 1 in which the transparent flexible polyurethane outer cladding 21 comprises UV inhibitors and covers the transparent flexible polyurethane inner fibre 20 to provide UV protection for the inner fibre.

In one embodiment, the inner fibre 20 and outer cladding 21 are co-extruded and the inner fibre and outer cladding are coaxial. The outer cladding 21 has a thickness that is less than the thickness of the inner fibre to maintain the desired transmission and side-leakage properties. To minimise the effect of the outer cladding 21 on the transmission and side-leakage properties, in a preferred embodiment, the thickness of the outer cladding 21 is substantially less than the thickness of the inner fibre 20, as shown in FIG. 7.

The inventor has recognized that an outer cladding of UV resistant, transparent, flexible polyurethane can also be employed with other light transmitting materials such as polycarbonate, which in at least some forms is also susceptible to deterioration when exposed to UV radiation. Whilst the outer cladding may be co-extruded with a central core of polycarbonate, problems can be encountered in achieving a sufficiently thin layer for some applications. Therefore, in one embodiment, the outer cladding of UV resistant polyurethane can be applied as a thin coating.

The invention finds numerous uses in novelty applications where a flexible light guide, which gives off a glow or side illumination, is required. Such applications include but are not limited to: footwear including laces; weaved into textiles for clothing; power cord illumination; adornments such as necklaces and hand bags; safety apparel such as bike helmets and hard hats; and toys. The invention also finds more practical applications, such as the dental suction tube, and outdoor applications, as described above.

Throughout the specification the aim has been to describe the invention without limiting the invention to any particular combination of alternate features and persons skilled in the art may envisage variations to the features described that will nonetheless fall within the scope of the invention.

The invention claimed is:

1. A light guide formed from an unclad flexible polyurethane fibre, wherein said light guide is extruded under non-optimum conditions to create imperfections in the light guide that produce significant side scattering over distances of up to several meters.

2. The light guide of claim 1, wherein the polyurethane fibre is a solid fibre.

3. The light guide of claim 1, wherein the polyurethane fibre is a tube.

4. The light guide of claim 1, wherein the polyurethane fibre further comprises light scattering particles.

5. An illuminated shoe lace comprising the unclad flexible polyurethane fibre of claim 1 and one or more light emitting diodes coupling light into said fibre.

6. A safety indicator for a power cord comprising:
an unclad flexible polyurethane tube extruded under non-optimum conditions to create imperfections in the tube that produce significant side scattering over distances of up to several meters; and one or more light emitting diodes coupling light into said tube.

7. An illuminated dental suction tube comprising an unclad polyurethane tube extruded under non-optimum conditions to create imperfections producing significant side scattering and one or more light emitting diodes coupling light into said tube for the illumination of a patient's mouth and for the extraction of fluids from the patient's mouth through the tube.

8. The illuminated dental suction tube of claim 7, wherein the unclad polyurethane tube is flexible, semi-rigid or rigid.

9. A dental curing tip comprising an unclad polyurethane solid fibre extruded under non-optimum conditions to create imperfections in the fibre that produce significant side scattering and one or more light sources coupling blue light into the fibre for curing fillings in teeth.

10. The dental curing tip of claim 9, wherein the unclad polyurethane extruded solid fibre is flexible, semi-rigid or rigid.

11. A light guide formed from a transparent flexible polyurethane inner fibre extruded under non-optimum conditions to create imperfections producing significant side scattering in the fibre and having a transparent flexible polyurethane outer cladding, wherein said inner fibre is susceptible to deterioration caused by ultra-violet (UV) radiation and said outer cladding is resistant to deterioration caused by ultra-violet (UV) radiation.

12. The light guide of claim 11, wherein the inner fibre and outer cladding are co-extruded.

13. The light guide of claim 11, wherein the inner fibre and outer cladding are coaxial.

14. The light guide of claim 11, wherein the outer cladding has a thickness less than the thickness of the inner fibre.

15. The light guide of claim 11, wherein the thickness of the outer cladding is substantially less than the thickness of the inner fibre.

16. A method of manufacturing the light guide of claim 1, wherein the light guide is extruded at a rate that is too slow or too fast compared with conventional extruding parameters.

* * * * *